(12) United States Patent
Reetz et al.

(10) Patent No.: US 7,265,237 B2
(45) Date of Patent: Sep. 4, 2007

(54) CHIRAL MONOPHOSPHITES AS LIGANDS FOR ASYMETRICAL SYNTHESIS

(75) Inventors: Manfred T. Reetz, Mülheim an der Ruhr (DE); Gerlinde Mehler, Mülheim an der Ruhr (DE); Andreas Meiswinkel, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 10/297,315

(22) PCT Filed: Jun. 5, 2001

(86) PCT No.: PCT/EP01/06344

§ 371 (c)(1),
(2), (4) Date: Dec. 4, 2002

(87) PCT Pub. No.: WO01/94278

PCT Pub. Date: Dec. 13, 2001

(65) Prior Publication Data

US 2003/0171608 A1    Sep. 11, 2003

(30) Foreign Application Priority Data

Jun. 6, 2000    (DE) ................. 100 27 505

(51) Int. Cl.
C07C 253/00    (2006.01)
(52) U.S. Cl. .............. 558/348; 556/13; 564/415; 564/489; 568/885
(58) Field of Classification Search ........... 568/12, 568/885; 560/1, 129, 155, 179, 303; 558/303, 558/348; 549/5, 6, 200, 206, 3, 216; 548/402, 548/413; 556/13; 564/415, 489
See application file for complete search history.

(56) References Cited

U.S. PATENT DOCUMENTS

| | | | |
|---|---|---|---|
| 4,605,692 A | * | 8/1986 | Spivack et al. ............ 524/117 |
| 5,360,938 A | * | 11/1994 | Babin et al. ............... 568/449 |
| 5,543,536 A | * | 8/1996 | Tam ........................... 556/13 |
| 5,618,871 A | * | 4/1997 | Nesvadba .................. 524/326 |
| 6,232,263 B1 | * | 5/2001 | Tolleson et al. .......... 502/213 |

FOREIGN PATENT DOCUMENTS

| | | |
|---|---|---|
| WO | 93 03839 A | 3/1993 |
| WO | 95 29153 A | 11/1995 |

OTHER PUBLICATIONS

CA:125:222113 abs of Organometallics by Bedford et al 15(19) pp. 3990-3997 1996.*
Chem Soc Chem Comm by Baker et al 18 pp. 1292-1293 1991.*
Angewandte Chemie by Reetz et al 39 (21) pp. 3889-3890 Nov. 2000.*
Scherer et al., Chirale tripod-rhodium-komplexe: Ligandsynthese, komplexchemie, katalyse, Journal of Organometallic Chemistry, 520, 1-2, 45-58, 1996.*
Pamies O. et al., "Synthesis and coordination chemistry of novel chiral P,S- ligands with a xylofuranose backbone: use in asymmetric hydroformylation and hydrogenation", Organometallics, 2000, vol. 19, No. 8, pp. 1488-1496.
Baker, M.K. et al., "Chiral aryl diphosphites: a new class of ligands for hydrocyanation catalysis", Chemical Communications, 1991, No. 18, pp. 1292-1293.
Reetz, M.T. et al., "Highly enatioselective Rh-catalyzed hydrogenation reactions based on chiral monophosphite ligands", Angewandte Chemie. Int't Ed., 2000, vol. 39, No. 21, pp. 3889-3890.

* cited by examiner

*Primary Examiner*—Thurman K. Page
*Assistant Examiner*—Chukwuma Nwaonicha
(74) *Attorney, Agent, or Firm*—Norris McLaughlin & Marcus PA

(57) ABSTRACT

Certain chiral monophosphites and their monothio derivatives are suitable as ligands in the asymmetrical transition-metal-catalyzed hydrogenation, hydroborination and hydrocyanation of prochiral olefins, ketones and imines.

10 Claims, No Drawings

CHIRAL MONOPHOSPHITES AS LIGANDS FOR ASYMETRICAL SYNTHESIS

This application is a 371 of PCT/EP01/06344, filed Jun. 5, 2001, and claims priority under 35 USC § 119 on the basis of German Application No. 100 27 505.2, filed Jun. 6, 2000.

The present invention involves the surprising result that certain chiral monophosphites and their monothio derivatives are excellent ligands in the asymmetrical transition-metal-catalyzed hydrogenation, hydroborination and hydrocyanation of prochiral olefins, ketones and imines.

The catalytic enantioselective synthesis has gained industrial importance in the last 20 years, for example, transition-metal-catalyzed asymmetrical hydrogenation (B. Cornils, W. A. Herrmann, *Applied Homogeneous Catalysis with Organometallic Compounds*, Wiley-VCH, Weinheim, 1996; R. Noyori, *Asymmetric Catalysis in Organic Synthesis*, Wiley, New York, 1994). As catalysts, there are usually employed rhodium, ruthenium or iridium complexes of optically active diphosphanes, such as BINAP (R. Noyori et al., *J. Am. Chem. Soc.* 1980, 102, 7932), DuPHOS (M. J. Burk et al., *J. Am. Chem. Soc.* 1995, 117, 9375), BICP (X. Zhang et al., *J. Am. Chem. Soc.* 1997, 119, 1799) and BPE (M. J. Burk et al., *J. Am. Chem. Soc.*, 1996, 118, 5142). A disadvantage of these systems is the relatively high preparative expenditure in their preparation and, when necessary, optical resolution of the racemic ligands, and the often insufficient enantioselectivity observed in the catalysis. In addition, phosphanes are sensitive towards oxidation, i.e., they relatively readily react with atmospheric oxygen, resulting in destruction of the ligand. Therefore, it is the object of industrial and academic research to prepare new and particularly well performing ligands in as simple a way as possible.

Certain chiral diphosphinites (T. V. RajanBabu, et. al., *J. Org. Chem.* 1997, 62, 6012) and diphosphonites (M. T. Reetz, A. Gosberg, R. Goddard, S.-H. Kyung, *Chem. Commun.* (*Cambridge*) 1998, 2077) have also been employed as ligands in transition-metal-catalyzed hydrogenation. In contrast, little is known about chiral diphosphites as ligands in such reactions. Some diphosphites derived from carbohydrates or tartaric acid result in poor enantioselectivities in the Rh-catalyzed hydrogenation of prochiral olefins (ee=1-34%) (H. Brunner et al., *J. Chem. Res. Synop.* 1980, 76; D. J. Wink et al., *Inorg. Chem.* 1990, 29, 5006). This is regrettable because phosphites are known to be significantly less sensitive to oxidation than phosphanes, and consequently, they need not be permanently handled under exclusion of air, i.e., under inert gas conditions. Therefore, it appeared interesting to learn that certain chiral diphosphites derived from dianhydro-D-mannitol in part yield very high enantioselectivities in the Rh-catalyzed hydrogenation of prochiral olefins (ee up to 98%) (M. T. Reetz, T. Neugebauer, *Angew. Chem.* 1999, 111, 134; *Angew. Chem., Int. Ed.* 1999, 38, 179). However, there is a disadvantageous result in that so high an enantioselectivity is exceptional, and in particular, that the dianhydro-D-mannitol is relatively difficult to obtain and consequently expensive.

These drawbacks do not apply to the present invention in which chiral monophosphites and their monothio derivatives are used as ligands in the asymmetrical hydrogenation, hydroborination and hydrocyanation of prochiral olefins, ketones and imines.

The synthesis of these chiral ligands has been described in several publications (see, e.g., U.S. Pat. No. 5,962,744A; WO9529153A1; WO9303839A1; U.S. Pat. No. 4,599,206). Their modular structure allows the preparation of a wide variety of novel chiral monophosphites in an enantiomerically pure form.

However, the use of chiral monophosphites as ligands in metal-catalyzed hydroformylation (see, e.g., WO9529153A1), hydrosilylation (see, e.g., U.S. Pat. No. 5,360,938; WO9303839A1), cyclopropanation (see, e.g., U.S. Pat. No. 5,360,938; WO9303839A1) and aldol addition (see, e.g., U.S. Pat. No. 5,360,938; WO9303839A1) did not result in any remarkable enantioselectivities in any of these cases (ee=10-26%). Nothing is known about the use of chiral monophosphites in hydrogenations. Although there are speculations (U.S. Pat. No. 5,360,938; WO9303839A1), these are not supported by experiments. In addition, the ee values obtained there are below 26% in all cases in hydrosilylation, cyclopropanation and aldol addition. Those skilled in the art considered that bidentate or chelating ligands which limit the degrees of freedom are required to enable high and industrially useful enantioselectivities (see, e.g., I. V. Komarov, A. Börner, *Angew. Chem.* 2001, 113, 1237; *Angew. Chem. Int. Ed.* 2001, 40, 1197; E. N. Jacobsen, A. Pfaltz, H. Yamamoto, *Comprehensive Asymmetric Catalysis*, Springer, Berlin, 1999).

While the initially described chiral diphosphites and the "standard ligands" of the BINAP, DuPHOS and PennPHOS types (E. N. Jacobsen, A. Pfaltz, H. Yamamoti, *Comprehensive Asymmetric Catalysis*, Springer, Berlin, 1999) and mixed ligands, such as phosphane-phosphites or phosphonite-phosphites (M. T. Reetz, M. Pastó, *Tetrahedron Lett.* 2000, 41, 3315) are chelating in nature, and due to this property, yield high enantioselectivities, the ligands of the present invention are not chelating compounds having two donor sites.

Surprisingly, it has now been found that just the above described monophosphites and their analogous monothio derivatives are excellent ligands in asymmetrical transition-metal-catalyzed hydrogenation and result in high enantioselectivities. The ee values obtained are very often above 90%. Not only are the ligands easily prepared, but they also have a relatively high oxidation resistance.

In detail, the invention comprises monosphosphites (Y=O) and their monothio derivatives (Y=S) of types I to IV as ligands.

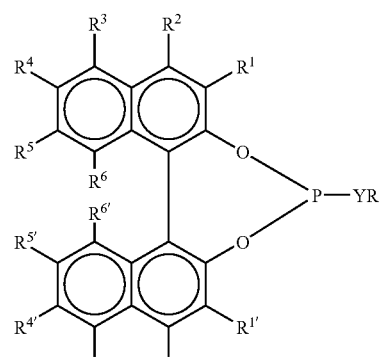

I

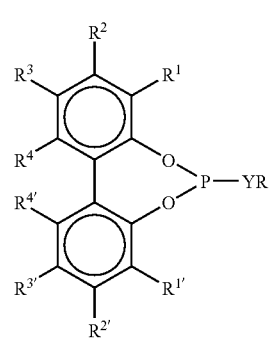

II

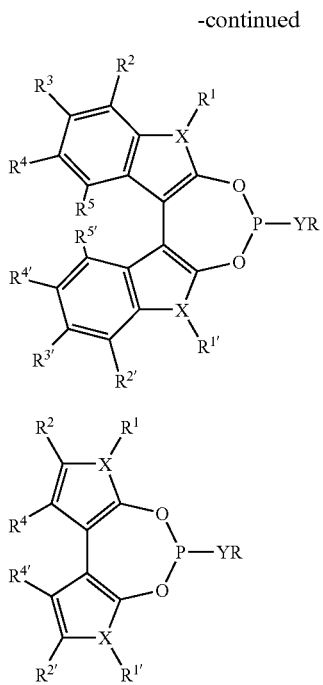

In the case of ligand class I, the compounds contain an axially chiral unit derived from binaphthyl with residues $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ which may independently represent the following groups: hydrogen (H), saturated hydrocarbons, optionally also functionalized and/or bridging (e.g., $R^1+R^2=-(CH_2)_4-$), aromatic or heteroaromatic groups, which may also be functionalized and/ or anellated and thus represent cyclic residues (for example, $R^1+R^2=R^{1'}+R^{2'}=$ortho-phenylene; corresponding to 4,4'-dihydroxy-5,5'-bis(phenanthryl)), non-aromatic unsaturated hydrocarbons, such as alkinyl groups —C≡CR', which may also be functionalized, silyl groups, such as —SiMe$_3$, halogens (—Cl, —Br, —F, —I), nitro (—NO$_2$) or nitrile groups (—CN), in addition to esters (—CO$_2$R'), carbonyls (—C(O)R'), amides (—C(O)NR'R''), amines (—NR'R''), ethers (—OR'), alkoxy (—OR'), sulfides (—SR') and selenides (—SeR') in which R' and R'' are hydrogen, saturated or non-aromatic unsaturated hydrocarbons, which may also be functionalized, or aromatic residues, which may also be functionalized. In particular, the present invention also includes all combinations of the mentioned residues for $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ including all $C_1$- and $C_2$-symmetrical substitution patterns of the binaphthyl core. Further, one or more carbon atoms of the binaphthyl core may be replaced by heteroatoms, such as Si, O, S or N. Preferably, binaphthyl itself ($R^1=R^2=R^3=R^4=R^5=R^6=R^{1'}=R^{2'}=R^{3'}=R^{4'}=R^{5'}=R^{6'}=H$) serves as an axially chiral element.

In the case of the class of compounds II, the axially chiral unit is a configuratively stable biphenyl derivative. Configurative stability with respect to axial chirality is ensured if $R^4 \neq H$ and $R^{4'} \neq H$ (E. L. Eliel, S. H. Wilen, L. N. Mander, *Stereochemistry of Organic Compounds*, Wiley, New York, 1994). $R^1$ to $R^4$ and $R^{1'}$ to $R^{4'}$ have the same latitude of variation as the residues $R^1$ to $R^6$ and $R^{1'}$ to $R^{6'}$ in the case of class of compounds I. Preferably, however, $R^1=R^2=R^{1'}=R^{2'}=H$ and $R^3+R^4=R^{3'}+R^{4'}=-(CH_2)_4-$ (corresponding to 5,5'-6,6'-7,7'-8,8'-octahydro-1,1'-binaphthyl, D.

J. Cram et al., *J. Org. Chem.* 1978, 43, 1930). In ligands of type II, one or more carbon atoms of the biphenyl core may also be replaced by heteroatoms, such as Si, O, S or N.

In the case of the class of compounds III, the compounds contain an axially chiral unit derived from 3,3'-bis(indolyl) (X=N), 3,3'-bis(benzo[b]thiophenyl) (X=S) or 3,3'-bis(benzo[b]furanyl) (X=O). In these cases too, the substituents $R^1$ to $R^5$ and $R^{1'}$ to $R^{5'}$ have the same latitude of variation as the residues $R^1$ to $R^6$ and $R^{1'}$ to $R^{6'}$ in the case of the class of compounds I. The substituents $R^1$ and $R^{1'}$ are omitted in the cases where X=O and X=S.

In the case of the class of compounds IV, the compounds contain as an axially chiral unit a configuratively stable heteroaromatic system derived from 3,3'-bis(pyrrolyl) (X=N), 3,3'-bis(thiophenyl) (X=S) or 3,3'-bis(furanyl) (X=O), which is also known, as an axially chiral unit. With respect to residues $R^1$, $R^2$, $R^4$, $R^{1'}$, $R^{2'}$ and $R^{4'}$, there are the same possible variations as has been described for the residues $R^1$ to $R^5$ and $R^{1'}$ to $R^{5'}$ of the class of compounds III.

In the case of the classes of compounds II and IV, it may also hold that $R^4=R^{4'}=H$. In this case, a configuratively labile axial element is obtained, and chirality is achieved by using a chiral residue R.

The present invention includes all stereoisomeric forms of compounds I-IV.

In the chiral phosphites I-IV, the residue R is derived from achiral or chiral alcohols, phenols or hydroxyheteroaromatics (Y=O) or their sulfur analogues (Y=S) (V), all of which may optionally bear additional functional groups, such as amino, ether, thioether, halogen or ester residues.

$$RYH \qquad\qquad V$$

In the simplest case, these are common alcohols (Y=O), such as methanol, ethanol, propanol or isopropanol etc., i.e., achiral alcohols consisting of $C_1$ to $C_{50}$ moieties. However, there may also be used chiral alcohols, such as 1-phenylethanol, terpene, carbohydrate or steroid alcohols. Few examples of such monophosphites are known from the literature, for example, I with $R^1=R^2=R^3=R^4=R^5=R^6=R^{1'}=R^{2'}=R^{3'}=R^{4'}=R^{5'}=R^{6'}=H$ and R=menthyl (P. H. Dussault et al., *J. Org. Chem.* 1997, 62, 1556). Functionalized alcohols, such as β-aminoalcohols or α-hydroxycarboxylate esters, are also possible. R may also represent an aromatic residue, and in these cases, RYH (V) means phenol-like compounds, typically phenol or α- or β-naphthol or substituted derivatives thereof, such as p-, m-, o-, alkyl-, aryl-, amino-, chloro-, bromo-, cyano-phenol. Compound I with $R^1=R^2=R^3=R^4=R^5=R^6=R^{1'}=R^{2'}=R^{3'}=R^{4'}=R^{5'}=R^{6'}=H$ and R=phenyl is known from the literature (K. Fuji et al., *Chem. Commun. (Cambridge)* 1999, 2289). RYH (V) may also represent a hydroxyheteroarene, such as 2-, 3- and 4-hydroxypyridine, 2-, 3-hydroxyfurane or 2-, 3-hydroxythiophene.

For the corresponding sulfur compounds (Y=S), achiral as well as chiral thiols V may be employed. The residue R may be varied here in the same way as has been described for the alcohols.

To be able to perform the asymmetrical hydrogenations, hydroborinations and hydrocyanations according to the invention, catalysts or precatalysts must be prepared first by reacting the chiral monophosphites with suitable transition metal salts (especially metals of groups VIII and Ib of the Periodic Table). Typical representatives include the following compounds, with cod=$\eta^2,\eta^2$-1,5-cyclooctadiene and cymol=$\eta^6$-1-iso-propyl-4-methylbenzene:
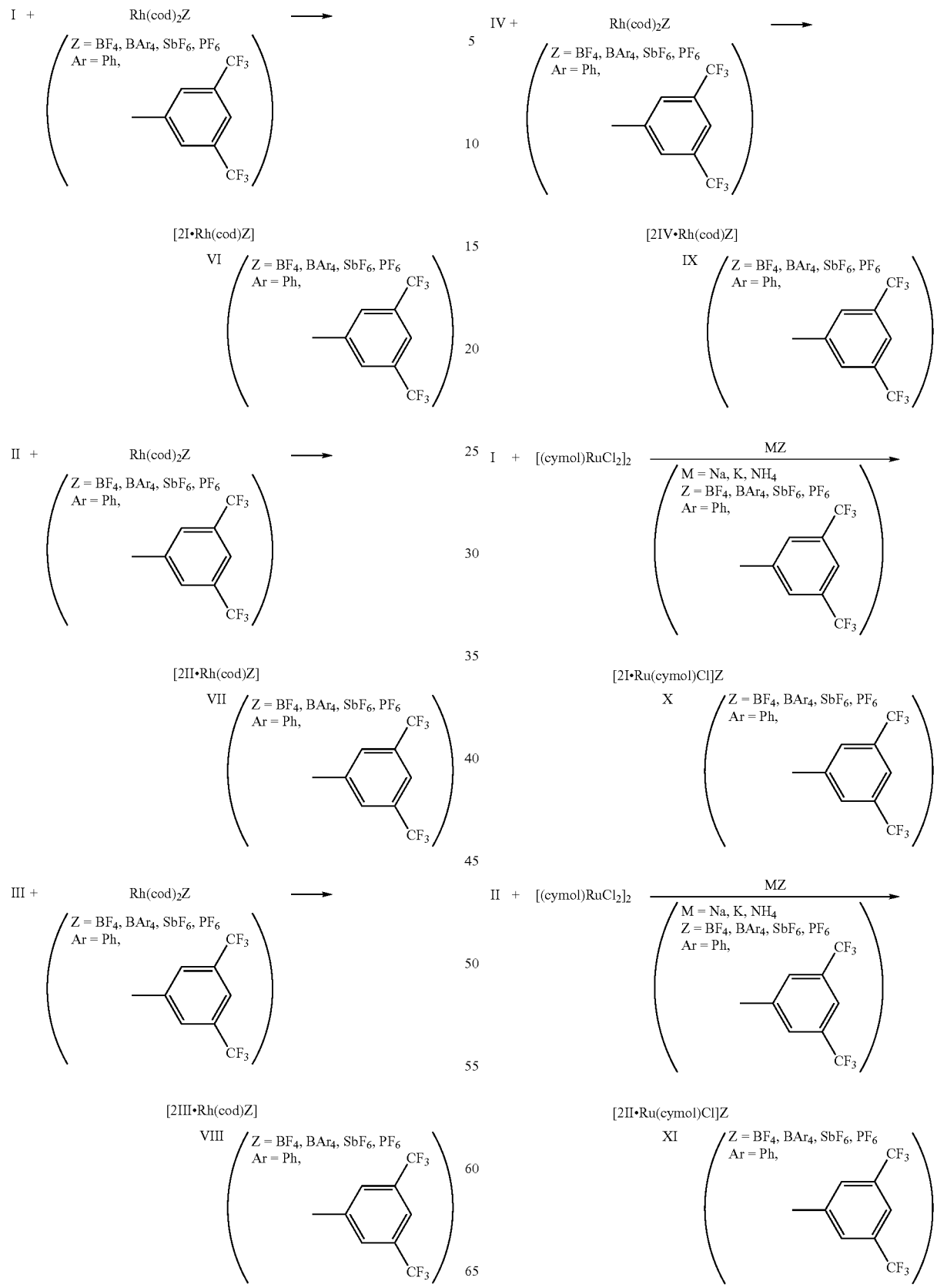

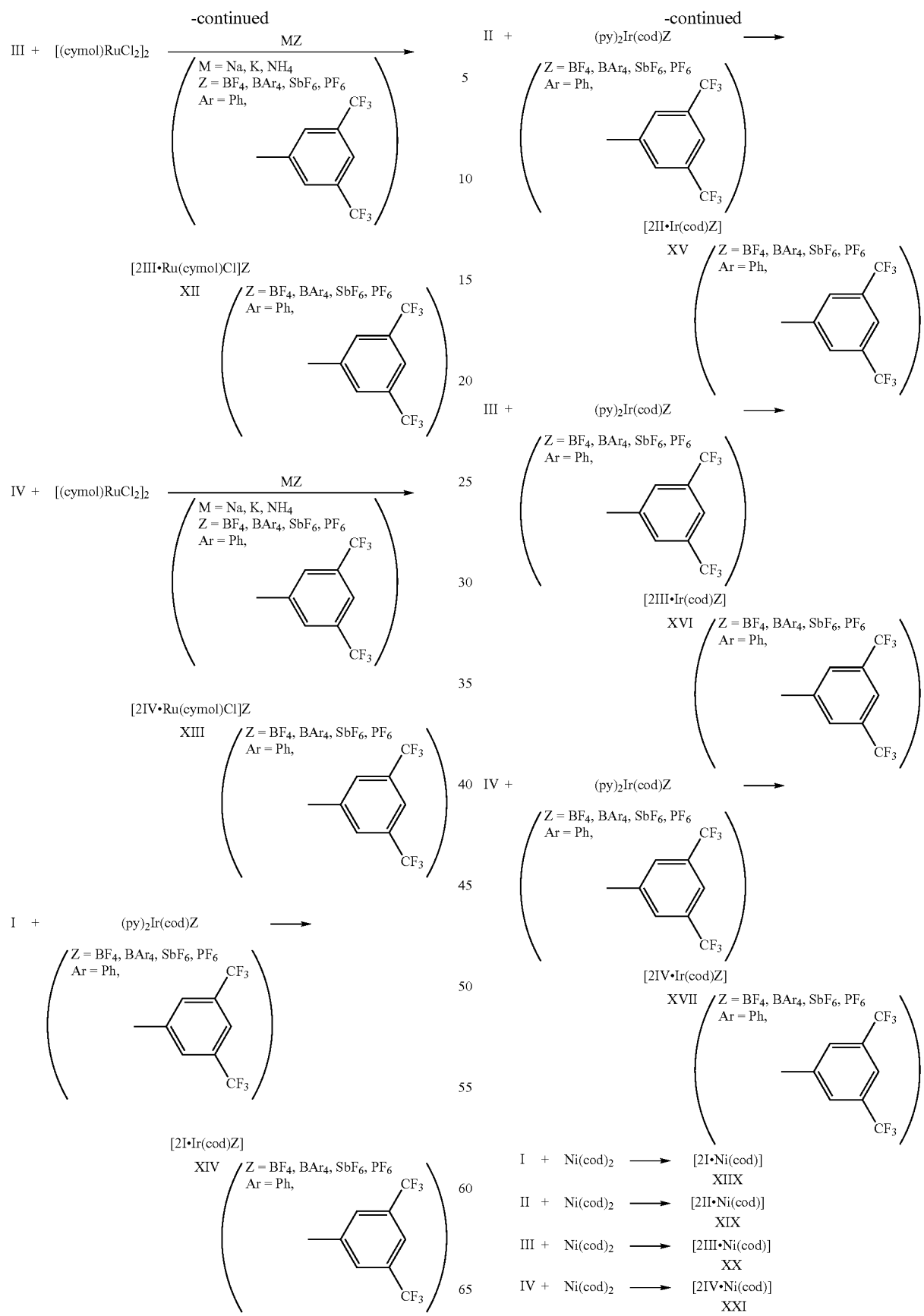

-continued

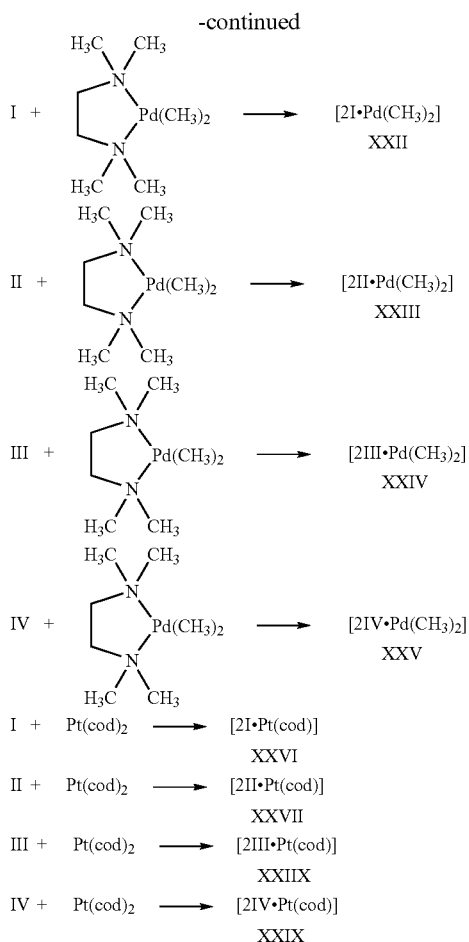

These catalysts or precatalysts are not the only possibilities, but rather the cationic forms of the transition metal compounds which are usual in literature may also be used, for example.

Thus, the invention includes the application of such metal complexes in asymmetrical hydrogenation, hydrocyanation and hydroboration, especially of prochiral olefins, ketones and imines. For illustration, the following reactions may be mentioned as typical examples. Such products are industrially valuable, for example, as building blocks in the synthesis of chiral active substances (drugs, plant protective agents, etc.).

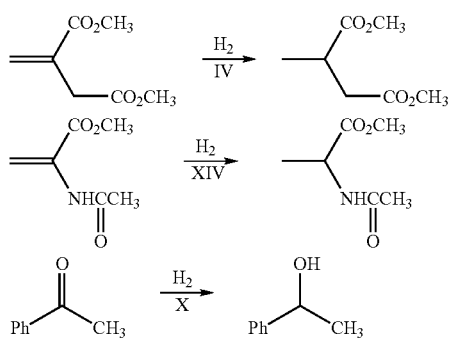

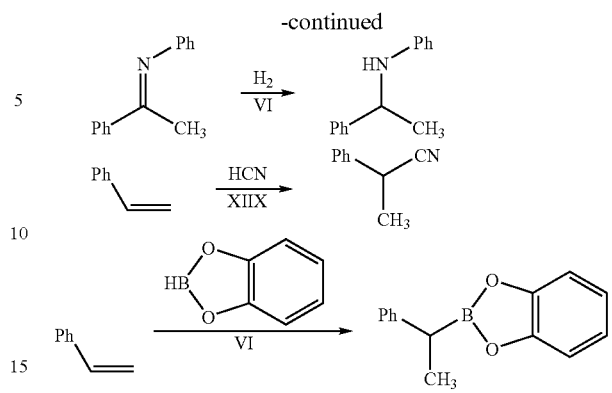

The invention will be illustrated without being limited by the following Examples:

Preparation of Monophosphite Ligands

EXAMPLE 1

Synthesis of (S)-2,2'-binaphthylphosphite Isopropyl Ester (I: $R^1=R^2=R^3=R^4=R^5=R^6=R^{1'}=R^{2'}=R^{3'}=R^{4'}=R^{5'}=R^{6'}=H$; Y=O; R=CH(CH$_3$)$_2$)

At room temperature, 0.751 g (2.1 mmol) of (S)-2,2'-binaphthyl phosphite ester chloride was charged in 100 ml of abs. diethyl ether. Thereto were pipetted 160 µl (0.126 g, 2.1 mmol) of abs. isopropanol and 0.29 ml (0.212 g, 2.3 mmol) of abs. triethylamine at room temperature. After stirring over night, the precipitated colorless solid was filtered over a D4 frit and washed with 5 ml of abs. diethyl ether. Subsequently, the filtrate was completely freed from solvent to obtain 0.60 g (1.6 mmol, 74.9%) of product as a colorless powder. Analysis: $^1$H NMR (CD$_2$Cl$_2$, 300 MHz): 7.88-7.12 [12H], 4.41 (m) [1H], 1.21 (d) J=6.15 Hz [3H]; 1.16 (d) J=6.18 Hz [3H]; $^{13}$C NMR (CD$_2$Cl$_2$, 75 Hz): 68.89 (d), J=13.6 Hz; 23.70 (d) J=3.2 Hz, 23.37 (d) J=4.0 Hz; $^{31}$P NMR (CD$_2$Cl$_2$, 121 MHz): 147.600(s); MS (EI, evaporation temperature 100° C.): m/z=374 (100%), 313 (22.5%), 239 (68.6%); EA: C: 73.21% (calc. 73.79%), H: 4.88% (calc. 5.11%), P: 8.67% (calc. 8.27%).

EXAMPLE 2

Synthesis of (S)-2,2'-binaphthylphosphite [(S)-1-phenylethyl] Ester (I: $R^1=R^2=R^3=R^4=R^5=R^6=R^{1'}=R^{2'}=R^{3'}=R^{4'}=R^{5'}=R^{6'}=H$; Y=O; R=(S)-1-phenylethyl)

At room temperature, 0.51 g (1.50 mmol) of (S)-2,2'-binaphthylphosphite ester chloride was charged in 100 ml of abs. diethyl ether. Thereto were pipetted 180 µl (0.183 g, 1.50 mmol) of abs. (S)-(−)-1-phenylethanol and 0.23 ml (0.167 g, 1.65 mmol) of abs. triethylamine at room temperature. After stirring over night, the precipitated colorless solid was filtered over a D4 frit and washed with 5 ml of abs. diethyl ether. Subsequently, the filtrate was completely freed from solvent to obtain 0.44 g (1.0 mmol, 66.6%) of product as a colorless powder. Analysis: $^1$H NMR (CD$_2$Cl$_2$, 300 MHz): 7.84-7.04 [17H], 5.27 (m) [1H], 1.44 (d) J=6.5 Hz [3H]; $^{13}$C NMR (CD$_2$Cl$_2$, 75 MHz): 65.25, 24.90 (d) J=3.1

Hz; $^{31}$P NMR (CD$_2$Cl$_2$, 121 MHz): 144.80(s); EA: C: 69.85% (calc. 77.05%), H: 5.95% (calc. 4.85%), P: 7.07% (calc. 7.09%).

EXAMPLE 3

Synthesis of (R)-2,2'-binaphthylphosphite Neopentyl Ester (I: R$^1$=R$^2$=R$^3$=R$^4$=R$^5$=R$^6$=R$^{1'}$=R$^{2'}$=R$^{3'}$=R$^{4'}$=R$^{5'}$=R$^{6'}$=H; Y=O; R=CH$_2$C(CH$_3$)$_3$)

At room temperature, 0.67 g (1.90 mmol) of (R)-2,2'-binaphthylphosphite ester chloride was charged in 100 ml of abs. toluene. Thereto were pipetted 0.5 ml (0.36 g, 3.67 mmol) of abs. triethylamine and 0.17 g (1.90 mmol) of neopentanol dissolved in 15 ml of abs. toluene at room temperature. After stirring over night, the precipitated colorless solid was filtered over a D4 frit and washed with 5 ml of abs. toluene. Subsequently, the filtrate was completely freed from solvent to obtain 0.72 g (1.79 mmol, 94.1%) of product as a colorless powder. Analysis: $^1$H NMR (CDCl$_3$, 300 MHz): 7.90-7.82 [4H], 7.45-7.14 [8H], 3.58 (m) [1H], 3.36 (m) [1H], 0.82 (s) [9H]; $^{31}$P NMR (CDCl$_3$, 121 MHz): 143.395 (s); MS (EI, evaporation temperature 110° C.): m/z=402 (73.49%), 332 (100%), 313 (18.69%), 268 (53.52%), 239 (28.97%); EA: C: 74.56% (calc. 74.62%), H: 5.72% (calc. 5.76%), P: 7.68% (calc. 7.70%).

EXAMPLE 4

Synthesis of (S)-2,2'-binaphthylphosphite (3-N,N-dimethylamino)-phenyl Ester (I: R$^1$=R$^2$=R$^3$=R$^4$=R$^5$=R$^6$=R$^{1'}$=R$^{2'}$=R$^{3'}$=R$^{4'}$=R$^{5'}$=R$^{6'}$=H; Y=O; R=C$_6$H$_4$N(CH$_3$)$_2$=3-N,N-dimethylaminophenyl)

At room temperature, 0.7 g (1.99 mmol) of (S)-2,2'-binaphthylphosphite ester chloride was charged in 100 ml of abs. diethyl ether. Thereto were pipetted 0.27 g (1.99 mmol) of abs. 3-N,N-dimethylaminophenol and 0.31 ml (0.22 g, 2,20 mmol) of abs. triethylamine at room temperature. After stirring over night, the precipitated colorless solid was filtered over a D4 frit and washed with 5 ml of abs. diethyl ether. Subsequently, the filtrate was completely freed from solvent to obtain 0.57 g (1.26 mmol, 63.5%) of product as a colorless powder. Analysis: $^1$H NMR (CD$_2$Cl$_2$, 300 MHz): 7.92-6.35 [16H], 2.72 (s) [6H]; $^{31}$P NMR (CD$_2$Cl$_2$, 121 MHz): 145.38 (d), J=85 Hz; MS (EI, evaporation temperature 150° C.): m/z 451 (100%), 315 (22.6%), 268 (44.4%); EA: C: 73.84% (calc. 74.49%), H: 5.68% (calc. 4.91%), N: 3.45% (calc. 3.10%), P: 6.17% (calc. 6.86%).

EXAMPLE 5

Synthesis of (S)-2,2'-binaphthylphosphite (N,N-di-iso-propylamino)ethyl Ester (I: R$^1$=R$^2$=R$^3$=R$^4$=R$^5$=R$^6$=R$^{1'}$=R$^{2'}$=R$^{3'}$=R$^{4'}$=R$^{5'}$=R$^{6'}$=H; Y=O; R=(CH$_2$)$_2$N(CH(CH$_3$)$_2$)$_2$=N,N-di-iso-propylaminoethyl)

At room temperature, 0.7 g (1.99 mmol) of (S)-2,2'-binaphthylphosphite ester chloride was charged in 100 ml of abs. diethyl ether. Thereto were pipetted 0.35 ml (0.29 g, 1.99 mmol) of abs. (N,N-di-iso-propylamino)ethanol and 0.31 ml (0.22 g, 2.20 mmol) of abs. triethylamine at room temperature. After stirring over night, the precipitated colorless solid was filtered over a D4 frit and washed with 5 ml of abs. diethyl ether. Subsequently, the filtrate was completely freed from solvent to obtain 0.52 g (1.13 mmol, 56.6%) of product as a colorless powder. Analysis: $^1$H NMR (CD$_2$Cl$_2$, 300 MHz): 7.89-7.10 [12H], 3.63(m) [2H], 2.79 (m) [2H], 2.51(t) [2H] J=7.3 Hz, 0.81 (d) [6H] J=4.9 Hz, 0.78 (d) [6H] J=4.9 Hz; $^{31}$P NMR (CD$_2$Cl$_2$, 121 MHz): 144.344 (d), J=85 Hz; EA: C: 72.79% (calc. 73.18%), H: 6.51% (calc. 6.58%), N: 2.99% (calc. 3.04%), P: 6.83% (calc. 6.74%).

EXAMPLE 6

(S)-2,2'-binaphthylphosphite [(S)-2-ethylcarboxy-2-ethyl] Ester (I: R$^1$=R$^2$=R$^3$=R$^4$=R$^5$=R$^6$=R$^{1'}$=R$^{2'}$=R$^{3'}$=R$^{4'}$=R$^{5'}$=R$^{6'}$=H; Y=O; R=(S)-CH(CH$_3$)CO$_2$CH$_2$CH$_3$)

At room temperature, 0.62 g (1.77 mmol) of (S)-2,2'-binaphthylphosphite ester chloride was charged in 100 ml of abs. toluene. Thereto were pipetted 0.50 ml (0.36 g, 3.67 mmol) of abs. triethylamine and 0.20 ml (0.21 g, 1.77 mmol) of (S)-lactate ethyl ester at room temperature. After stirring over night, the precipitated colorless solid was filtered over a D4 frit and washed with 5 ml of abs. toluene. Subsequently, the filtrate was completely freed from solvent to obtain 0.58 g (1.34 mmol, 75.8%) of product as a colorless powder. Analysis: $^1$H NMR (CDCl$_3$, 300 MHz): 7.92-7.80 [4H], 7.47-7.18 [8H], 4.62 (m) [1H], 4.16 (q) J=7.1 Hz [2H], 1.42 (d) J=6.9 Hz [3H], 1.21 (t) J=7.1 Hz [3H]; $^{31}$P NMR (CDCl$_3$, 121 MHz): 141.507 (s); MS (EI, evaporation temperature 130° C.): m/z=432 (87.41%), 331 (100%), 315 (31.30%), 268 (63.59%), 239 (31.11%); EA: C: 69.32% (calc. 69.44%), H: 4.04% (calc. 4.90%), P: 7.30% (calc. 7.16%).

EXAMPLE 7

Synthesis of (S)-2,2'-binaphthylphosphite (2-methoxy)ethyl Ester (I: R$^1$=R$^2$=R$^3$=R$^4$=R$^5$=R$^6$=R$^{1'}$=R$^{2'}$=R$^{3'}$=R$^{4'}$=R$^{5'}$=R$^{6'}$=H; Y=O; R=CH$_2$CH$_2$OCH$_3$)

At room temperature, 1.43 g (4.1 mmol) of (S)-2,2'-binaphthylphosphite ester chloride was charged in 100 ml of abs. diethyl ether. Thereto were pipetted 0.32 ml (0.31 g, 4.1 mmol) of 2-methoxyethanol and 0.59 ml (0.46 g, 4.50 mmol) of abs. triethylamine at room temperature. After stirring over night, the precipitated colorless solid was filtered over a D4 frit and washed with 5 ml of abs. diethyl ether. Subsequently, the filtrate was completely freed from solvent to obtain 0.92 g (2.35 mmol, 57.5%) of product as a colorless powder. Analysis: $^1$H NMR (CD$_2$Cl$_2$, 300 MHz): 7.87-7.08 [12H], 3.94 (m) [1H], 3.77 (m) [1H], 3.33(m) [2H], 3.21 (s) [3H]; $^{31}$P NMR (CD$_2$Cl$_2$, 121 MHz): 145.734 (s); MS (EI, evaporation temperature 135° C.): m/z=390 (100%), 331 (88.47%), 268 (65.78%); EA: C: 69.88% (calc. 70.76%), H: 5.49% (calc. 4.90%), P: 7.51% (calc. 7.93%).

EXAMPLE 8

Synthesis of 2,2'-biphenylphosphite [(S)-1-phenylethyl] Ester (II: R$^1$=R$^2$=R$^3$=R$^4$=R$^{1'}$=R$^{2'}$=R$^{3'}$=R$^{4'}$=H; Y=O; R=(S)-1-phenylethtyl)

At room temperature, 0.76 g (3.04 mmol) of 2,2'-biphenylphosphite ester chloride was charged in 100 ml of abs. toluene. Thereto were pipetted 1.00 ml (0.73 g, 7.22 mmol) of abs. triethylamine and 0.37 ml (0.37 g, 3.04 mmol) of (S)-1-phenylethanol at room temperature. After stirring over night, the precipitated colorless solid was filtered over a D4 frit and washed with 5 ml of abs. toluene. Subsequently, the filtrate was completely freed from solvent to obtain 1.00 g (2.97 mmol, 97.8%) of product as a yellow oil. Analysis: $^1$H NMR (CDCl$_3$, 300 MHz): 7.39-7.16 (m) [11H], 6.90-6.75 (m) [2H], 5.38 (m) [1H], 1.51 (d) J=6.5 Hz [3H]; $^{31}$P NMR (CDCl$_3$, 121 MHz): 142.870 (s); MS (EI, evaporation temperature 65° C.): m/z=336 (13.53%), 232 (99.23%), 168 (15.83%), 139 (7.90%), 105 (100%), 79 (9.82%); EA: C: 71.51% (calc. 71.42%), H: 5.16% (calc. 5.09%), P: 9.14% (calc. 9.21%).

EXAMPLE 9

Synthesis of (R)-2,2'-binaphthylphosphite Phenyl Monothioester (I: $R^1=R^2=R^3=R^4=R^5=R^6=R^{1'}=R^{2'}=R^{3'}=R^{4'}=R^{5'}=R^{6'}=H$; Y=S; R=phenyl)

At room temperature, 0.94 g (2.69 mmol) of (R)-2,2'-binaphthylphosphite ester chloride was charged in 100 ml of abs. toluene. Thereto were pipetted 0.38 ml (0.28 g, 2.73 mmol) of abs. triethylamine and 0.28 ml (0.30 g, 2.69 mmol) of thiophenol at room temperature. After stirring over night, the precipitated colorless solid was filtered over a D4 frit and washed with 5 ml of abs. toluene. Subsequently, the filtrate was completely freed from solvent to obtain 0.99 g (2.34 mmol, 87.0%) of product as a yellow powder. Analysis: $^1$H NMR (CDCl$_3$, 300 MHz): 7.95-7.86 [4H], 7.57-7.20 [13H]; $^{31}$P NMR (CDCl$_3$, 121 MHz): 217.733 (s); MS (EI, evaporation temperature 160° C.): m/z=424 (37.93%), 315 (100%), 268 (67.93%), 252 (26.63%), 239 (41.16%), 110 (10.85%); EA: C: 73.15% (calc. 73.57%), H: 3.88% (calc. 4.04%), P: 7.15% (calc. 7.30%).

Preparation of Metal Complexes

EXAMPLE 10

Synthesis of ($\eta^2,\eta^2$-cycloocta-1,5-diene)[(S)-2,2'-binaphthylphosphite (R)-(1-phenyl)ethyl Ester] rhodium(I) Tetrafluoroborate At room temperature, 0.244 g (0.56 mmol) of [(S)-2,2'-binaphthylphosphite (R)-(1-phenyl)ethyl ester] and 0.277 g (0.56 mmol) of bis(1,5-cyclooctadiene)rhodium(I) tetrafluoroborate were stirred in 30 ml of abs. dichloromethane for 20 h. Subsequently, the orange solution was completely freed from solvent. The residue was taken up in 20 ml of abs. diethyl ether, and the precipitated solid was filtered over a D4 frit to obtain 0.21 g (0.29 mmol, 51.7%) of product as a red-orange powder. Analysis: $^{31}$P NMR (CD$_2$Cl$_2$, 121 MHz): 137.520 (d, $^1$J$_{RhP}$=247 Hz); EA: C: 59.80% (calc. 58.88%), H: 5.18% (calc. 4.53%), P 4.18% (calc. 4.21%), Rh 14.16% (calc. 14.01%).

EXAMPLE 11

Synthesis of ($\eta^2,\eta^2$-cycloocta-1,5-diene)bis[(S)-2,2'-binaphthylphosphite [(S)-2-butyl]ester]rhodium(I) Tetrafluoroborate ([Rh(cod)(I)$_2$]BF$_4$ with I: $R^1=R^2=R^3=R^4=R^5=R^6=R^{1'}=R^{2'}=R^{3'}=R^{4'}=R^{5'}=R^{6'}=H$; Y=O; R=(S)-2-butyl; cod=$\eta^2,\eta^2$-cycloocta-1,5-diene)

At −78° C., 0.11 g (0.26 mmol) of Rh(cod)$_2$BF$_4$ was charged in 15 ml of dichloromethane, and a solution of 0.20 g (0.52 mmol) of (S)-2,2'-binaphthylphosphite [(S)-2-butyl] ester in 5 ml of dichloromethane was slowly added. The solution was slowly warmed to room temperature over 20 h, and the solvent was subsequently removed under vacuum. The remaining yellow oil was suspended in 5 ml of pentane and stirred for 24 h to form a yellow solid. The solvent was filtered off, and the solid was washed twice with 5 ml each of pentane and dried under vacuum to obtain 0.26 g (0.24 mmol, 92.3%) of product as a yellow powder. Analysis: $^1$H NMR (CD$_2$Cl$_2$, 300 MHz): 8.11-7.13 (m) [24H], 5.70 (m) [2H], 5.23 (m) [2H], 4.35 (m) [4H], 2.19-1.21 (m) [10H], 1.15 (d) J=6.1 Hz [6H], 0.91 (t) J=7.4 Hz [6H]; $^{31}$P NMR (CD$_2$Cl$_2$, 121 MHz): 119.983 (d) J=257.6 Hz; MS (ESI/pos. in CH$_2$Cl$_2$): m/z=987 (100%) [M-BF$_4$], 877 (19.89%); EA: C: 62.28% (calc. 62.59%), H: 5.14% (calc. 5.06%), P: 5.74% (calc. 5.76%).

Hydrogenations

General Protocol for Hydrogenation with Preformed Catalyst

In a round-bottom flask with a lateral cock, 1.0 ml of a 1 mM solution of the stated catalyst in dichloromethane was charged. To this, 9.0 ml of a 0.11 M substrate solution in dichlormethane was added. The solution was now saturated with hydrogen and stirred for the stated time, t, at room temperature under 1.3 bar of hydrogen pressure. 2 ml of the thus obtained solution was filtered over 150 mg of silica (70-230 mesh, activity grade I) and analyzed by gas chromatography.

General Protocol for Hydrogenation with Catalyst Prepared in Situ

In a round-bottom flask with a lateral cock, 0.5 ml of a 2 mM solution of Rh(cod)$_2$BF$_4$ in dichloromethane was charged. To this, 0.5 ml of a solution of the stated ligand L having the stated concentration c was added, followed by 9.0 ml of a 0.11 M substrate solution in dichloromethane. The solution was now saturated with hydrogen and stirred for the stated time, t, at room temperature under 1.3 bar of hydrogen pressure. 2 ml of the thus obtained solution was filtered over 150 mg of silica (70-230 mesh, activity grade I) and analyzed by gas chromatography.

Enantioselective Hydrogenation of Dimethyl Itaconate with Preformed Catalyst

EXAMPLES 12-13

Examples 12-13 describe the hydrogenation of the substrate dimethyl itaconate to form 2-methylsuccinate dimethyl ester according to the "General protocol for hydrogenation with preformed catalyst". The exact reaction conditions and the conversions and enantioselectivities achieved are stated in Table 1.

TABLE 1

| | Catalyst[a] [Rh(cod)(L)$_2$]BF$_4$ | | | | |
|---|---|---|---|---|---|
| Ex. | Configuration of L | Residue R | Time t h | Conv. in %[b] | ee in % |
| 12. | (S) | (S)-CH(CH$_3$)CH$_2$CH$_3$ | 20 | 100 | 96.8 (S) |
| 13. | (S) | (R)-CH(CH$_3$)C$_6$H$_5$ | 20 | 100 | 94.0 (S) |

[a]These are catalysts [Rh(cod)(L)$_2$]BF$_4$ with ligands L of structure I with $R^1 = R^2 = R^3 = R^4 = R^5 = R^6 = R^{1'} = R^{2'} = R^{3'} = R^{4'} = R^{5'} = R^{6'} = H$ and Y = O.
[b]If an educt could no longer be detected by gas chromatography, 100% is stated as the conversion.

Enantioselective Hydrogenation of Dimethyl Itaconate with a Catalyst Prepared in Situ

EXAMPLES 14-55

Examples 14-55 describe the hydrogenation of the substrate dimethyl itaconate to form 2-methylsuccinate dimethyl ester according to the "General protocol for hydrogenation with catalyst prepared in situ". The exact reaction conditions and the conversions and enantioselectivities achieved are stated in Tables 2 to 4.

TABLE 3

| Ex. | Ligand L[a] Residues $R^3$ and $R^{3'}$ | Residue R | Conc. c | Time t h | Conv. in %[b] | ee in % |
|---|---|---|---|---|---|---|
| 52. | H | (S)-CH(CH$_3$)CH$_2$CH$_3$ | 4 mM | 20 | 100 | 11.8 (S) |
| 53. | H | (S)-CH(CH$_3$)C$_6$H$_5$ | 4 mM | 20 | 100 | 30.0 (R) |
| 54. | CH(CH$_3$)$_2$ | (S)-CH(CH$_3$)C$_6$H$_5$ | 4 mM | 20 | 100 | 15.6 (R) |

[a]These are ligands of the structure II with $R^1 = R^2 = R^4 = R^{1'} = R^{2'} = R^{4'}$ = H and Y = O.
[b]If an educt could no longer be detected by gas chromatography, 100% is stated as the conversion.

TABLE 2

| Ex. | Ligand L[a] Config. | Residue R | Conc. c | Time t h | Conv. in %[b] | ee in % |
|---|---|---|---|---|---|---|
| 14. | (S) | CH$_3$ | 2 mM | 20 | 100 | 89.2 (S) |
| 15. | (S) | CH$_3$ | 4 mM | 3 | 100 | 83.2 (S) |
| 16. | (S) | CH(CH$_3$)$_2$ | 2 mM | 20 | 100 | 97.6 (S) |
| 17. | (S) | CH(CH$_3$)$_2$ | 4 mM | 3 | 100 | 97.0 (S) |
| 18. | (S) | (rac)-CH(CH$_3$)C$_6$H$_5$ | 2 mM | 20 | 100 | 98.8 (S) |
| 19. | (S) | (rac)-CH(CH$_3$)C$_6$H$_5$ | 4 mM | 3 | 100 | 98.6 (S) |
| 20.[c] | (S) | (R)-CH(CH$_3$)C$_6$H$_5$ | 2 mM | 20 | 100 | 99.2 (S) |
| 21. | (S) | (R)-CH(CH$_3$)C$_6$H$_5$ | 4 mM | 3 | 100 | 98.8 (S) |
| 22. | (S) | (S)-CH(CH$_3$)C$_6$H$_5$ | 2 mM | 20 | 100 | 98.2 (S) |
| 23. | (S) | (S)-CH(CH$_3$)C$_6$H$_5$ | 4 mM | 3 | 100 | 96.8 (S) |
| 24. | (R) | (R)-CH(CH$_3$)C$_6$H$_5$ | 4 mM | 3 | 100 | 97.8 (R) |
| 25. | (R) | (R)-CH(CH$_3$)C$_6$H$_5$ | 2 mM | 20 | 100 | 96.6 (R) |
| 26. | (R) | (S)-CH(CH$_3$)C$_6$H$_5$ | 4 mM | 3 | 100 | 99.4 (R) |
| 27. | (R) | (S)-CH(CH$_3$)C$_6$H$_5$ | 2 mM | 20 | 100 | 96.8 (R) |
| 28. | (S) | CH(C$_6$H$_5$)$_2$ | 2 mM | 20 | 100 | 92.0 (S) |
| 29. | (S) | C$_6$H$_5$ | 2 mM | 20 | 100 | 96.6 (S) |
| 30. | (S) | C$_6$H$_5$ | 4 mM | 3 | 100 | 97.8 (S) |
| 31. | (S) | CH(CF$_3$)$_2$ | 4 mM | 20 | 55.0 | 72.0 (S) |
| 32. | (S) | (CH$_2$)$_4$CH$_3$ | 4 mM | 3 | 100 | 94.2 (S) |
| 33. | (S) | CH(CH$_2$CH$_2$)$_2$ | 4 mM | 3 | 100 | 97.4 (S) |
| 34. | (S) | CH(CH$_2$)$_4$ (cyclopentyl) | 4 mM | 3 | 100 | 99.0 (S) |
| 35. | (S) | Fluorenyl | 4 mM | 3 | 100 | 96.0 (S) |
| 36. | (S) | C(CH$_3$)$_3$ | 4 mM | 3 | 100 | 91.4 (S) |
| 37. | (S) | Naphthyl | 4 mM | 3 | 100 | 87.0 (S) |
| 38. | (S) | (-)-Menthyl | 4 mM | 3 | 100 | 94.8 (S) |
| 39. | (S) | (-)-Menthyl | 4 mM | 3 | 100 | 91.0 (S) |
| 40. | (S) | C$_6$H$_4$N(CH$_3$)$_2$ (3-N,N-dimethylaminophenyl) | 4 mM | 20 | 51.4 | 82.2 (S) |
| 41. | (S) | (CH$_2$)$_2$N(CH(CH$_3$)$_2$)$_2$ (N,N-diisopropylaminoethyl) | 4 mM | 20 | 100 | 84.6 (S) |
| 42. | (S) | CH$_2$C$_6$H$_5$ | 4 mM | 20 | 100 | 98.2 (S) |
| 43. | (S) | (S)-CH(CH$_3$)CH$_2$CH$_3$ | 4 mM | 20 | 100 | 98.5 (S) |
| 44. | (R) | (S)-CH(CH$_3$)CH$_2$CH$_3$ | 4 mM | 20 | 100 | 98.6 (R) |
| 45. | (S) | (S)-CHCH(CH$_3$)CH$_2$CH$_3$ | 4 mM | 20 | 100 | 64.4 (S) |
| 46. | (R) | (S)-CHCH(CH$_3$)CH$_2$CH$_3$ | 4 mM | 20 | 100 | 97.4 (R) |
| 47. | (R) | CH$_2$C(CH$_3$)$_3$ | 4 mM | 20 | 100 | 98.6 (R) |
| 48. | (S) | (S)-CH(CH$_3$)CO$_2$CH$_2$CH$_3$ | 4 mM | 20 | 100 | 91.0 (S) |
| 49. | (R) | (S)-CH(CH$_3$)CO$_2$CH$_2$CH$_3$ | 4 mM | 20 | 84.0 | 67.8 (R) |
| 50. | (S) | CH$_2$CH$_2$OCH$_3$ | 4 mM | 3 | 100 | 94.4 (S) |
| 51. | (R) | CH$_2$CH$_2$OCH$_3$ | 4 mM | 20 | 100 | 95.1 (R) |

[a]These are ligands of structure I with $R^1 = R^2 = R^3 = R^4 = R^5 = R^6 = R^{1'} = R^{2'} = R^{3'} = R^{4'} = R^{5'} = R^{6'}$ = H and Y = O.
[b]If an educt could no longer be detected by gas chromatography, 100% is stated as the conversion.
[c]When only 0.1 ml each or only 0.2 ml each of 2 mM Rh(cod)$_2$BF$_4$ solution and 2 mM ligand solution was used, after 20 h, the hydrogenation is quantitative and an enantiomeric excess (ee) of 99.40% each in favor of the S-configurated product is measured.

TABLE 4

| Ex. | Ligand L[a] Config. | Residue R | Conc. c | Time t h | Conv. in % | ee in % |
|---|---|---|---|---|---|---|
| 55. | (R) | $C_6H_5$ | 4 mM | 20 | 55.2 | 66.6 (R) |

[a]This is a ligand of structure I with $R^1 = R^2 = R^3 = R^4 = R^5 = R^6 = R^{1'} = R^{2'} = R^{3'} = R^{4'} = R^{5'} = R^{6'} = H$ and $Y = S$.

Enantioselective Hydrogenation of 2-acetamidoacrylare Methyl Ester with Preformed Catalyst

EXAMPLE 56

Example 56 describes the hydrogenation of the substrate 2-acetamidoacrylate methyl ester to form N-acetylalanine methyl ester according to the "General protocol for hydrogenation with preformed catalyst". The exact reaction conditions and the conversions and enantioselectivities achieved are stated in Table 5.

TABLE 5

| | Catalyst[a] $[Rh(cod)(L)_2]BF_4$ | | | | |
|---|---|---|---|---|---|
| Ex. | Configuration of L | Residue R | Time t h | Conv. in %[b] | ee in % |
| 56. | (S) | (S)-$CH(CH_3)CH_2CH_3$ | 20 | 100 | 94.8 (R) |

[a]This is a catalyst $[Rh(cod)(L)_2]BF_4$ with ligands L of structure I with $R^1 = R^2 = R^3 = R^4 = R^5 = R^6 = R^{1'} = R^{2'} = R^{3'} = R^{4'} = R^{5'} = R^{6'} = H$ and $Y = O$.
[b]If an educt could no longer be detected by gas chromatography, 100% is stated as the conversion.

Enantioselective Hydrogenation of 2-acetamidoacrylate Methyl Ester with a Catalyst Prepared in Situ

EXAMPLES 57-80

Examples 57-80 describe the hydrogenation of the substrate 2-acetamidoacrylate methyl ester to form N-acetylalanine methyl ester according to the "General protocol for hydrogenation with catalyst prepared in situ". The exact reaction conditions and the conversions and enantioselectivities achieved are stated in Tables 6 and 7.

TABLE 6

| | Ligand L[a] | | | Time | | |
|---|---|---|---|---|---|---|
| Ex. | Config. | Residue R | Conc. c | t h | Conv. in %[b] | ee in % |
| 57. | (S) | $CH_3$ | 2 mM | 20 | 100 | 72.8 (R) |
| 58. | (S) | $CH(CH_3)_2$ | 2 mM | 20 | 100 | 94.8 (R) |
| 59. | (S) | $CH(CH_3)_2$ | 4 mM | 3 | 100 | 93.0 (R) |
| 60. | (S) | (rac)-$CH(CH_3)C_6H_5$ | 2 mM | 20 | 100 | 99.9 (R) |
| 61. | (S) | (rac)-$CH(CH_3)C_6H_5$ | 4 mM | 3 | 100 | 92.4 (R) |
| 62. | (S) | (R)-$CH(CH_3)C_6H_5$ | 2 mM | 20 | 100 | 95.5 (R) |
| 63. | (S) | (R)-$CH(CH_3)C_6H_5$ | 4 mM | 3 | 100 | 95.6 (R) |
| 64. | (S) | (S)-$CH(CH_3)C_6H_5$ | 2 mM | 20 | 100 | 93.3 (R) |
| 65. | (S) | $C_6H_5$ | 2 mM | 20 | 100 | 80.6 (R) |
| 66. | (S) | $CH(CH_2CH_3)_2$ | 4 mM | 3 | 100 | 94.8 (R) |
| 67. | (S) | $CH(CH_2)_4$ (Cyclopentyl) | 4 mM | 3 | 100 | 96.6 (R) |
| 68. | (S) | $C(CH_3)_3$ | 4 mM | 3 | 100 | 95.4 (R) |
| 69. | (S) | $CH_2(C_6H_5)$ | 4 mM | 20 | 100 | 88.9 (R) |
| 70. | (S) | (S)-$CH(CH_3)CH_2CH_3$ | 4 mM | 20 | 100 | 95.6 (R) |

TABLE 6-continued

| | Ligand L[a] | | | Time | | |
|---|---|---|---|---|---|---|
| Ex. | Config. | Residue R | Conc. c | t h | Conv. in %[b] | ee in % |
| 71. | (R) | (S)-$CH(CH_3)CH_2CH_3$ | 4 mM | 20 | 100 | 95.6 (S) |
| 72. | (S) | (S)-$CHCH(CH_3)CH_2CH_3$ | 4 mM | 20 | 100 | 90.6 (R) |
| 73. | (R) | (S)-$CHCH(CH_3)CH_2CH_3$ | 4 mM | 20 | 100 | 92.8 (S) |
| 74. | (R) | $CH_2C(CH_3)_3$ | 4 mM | 20 | 100 | 93.0 (S) |
| 75. | (S) | (S)-$CH(CH_3)CO_2CH_2CH_3$ | 4 mM | 20 | 100 | 87.8 (R) |
| 76. | (R) | (S)-$CH(CH_3)CO_2CH_2CH_3$ | 4 mM | 20 | 84.0 | 73.0 (S) |
| 77. | (R) | $CH_2CH_2OCH_3$ | 4 mM | 20 | 100 | 88.2 (S) |

[a]These are ligands of structure I with $R^1 = R^2 = R^3 = R^4 = R^5 = R^6 = R^{1'} = R^{2'} = R^{3'} = R^{4'} = R^{5'} = R^{6'} = H$ and $Y = O$.
[b]If an educt could no longer be detected by gas chromatography, 100% is stated as the conversion.

TABLE 7

| | Ligand L[a] Residues | | | Time t | Conv. | ee |
|---|---|---|---|---|---|---|
| Ex. | $R^3$ and $R^{3'}$ | Residue R | Conc. c | h | in %[b] | in % |
| 78. | H | (S)-$CH(CH_3)CH_2CH_3$ | 4 mM | 20 | 100 | 10.0 (R) |
| 79. | H | (S)-$CH(CH_3)C_6H_5$ | 4 mM | 20 | 100 | 18.2 (R) |
| 80. | $CH(CH_3)_2$ | (S)-$CH(CH_3)C_6H_5$ | 4 mM | 20 | 100 | 22.8 (R) |

[a]These are ligands of structure II with $R^1 = R^2 = R^4 = R^{1'} = R^{2'} = R^{4'} = H$ and $Y = O$.
[b]If an educt could no longer be detected by gas chromatography, 100% is stated as the conversion.

Enantioselective Hydrogenation of (Z)-2-acetamidocinnamate Methyl Ester with a Catalyst Prepared in Situ

EXAMPLES 81-97

Examples 81-97 describe the hydrogenation of the substrate (Z)-2-acetamidocinnamate methyl ester to form N-acetylphenylalanine methyl ester according to the "General protocol for hydrogenation with catalyst prepared in situ". The exact reaction conditions and the conversions and enantioselectivities achieved are stated in Table 8.

TABLE 8

| | Ligand L[a] | | | Time | Conv. | ee |
|---|---|---|---|---|---|---|
| Ex. | Config. | Residue R | Conc. c | t h | in %[b] | in % |
| 81. | (S) | $CH_3$ | 4 mM | 20 | 100 | 53.0 (R) |
| 82. | (S) | $CH_3$ | 2 mM | 20 | 100 | 55.8 (R) |
| 83. | (S) | $CH(CH_3)_2$ | 4 mM | 3 | 100 | 87.2 (R) |
| 84. | (S) | $CH(CH_3)_2$ | 2 mM | 20 | 100 | 88.2 (R) |
| 85. | (S) | (S)-$CH(CH_3)C_6H_5$ | 4 mM | 3 | 98.9 | 85.0 (R) |
| 86. | (S) | (S)-$CH(CH_3)C_6H_5$ | 2 mM | 20 | 91.7 | 84.8 (R) |
| 87. | (S) | (R)-$CH(CH_3)C_6H_5$ | 4 mM | 3 | 97.2 | 88.6 (R) |
| 88. | (S) | (R)-$CH(CH_3)C_6H_5$ | 2 mM | 20 | 100 | 91.7 (R) |
| 89. | (S) | (rac)-$CH(CH_3)C_6H_5$ | 2 mM | 20 | 100 | 87.8 (R) |
| 90. | (R) | (S)-$CH(CH_3)C_6H_5$ | 2 mM | 20 | 100 | 92.2 (S) |
| 91. | (R) | (R)-$CH(CH_3)C_6H_5$ | 2 mM | 20 | 100 | 86.6 (S) |

TABLE 8-continued

| Ex. | Ligand L[a] Config. | Residue R | Conc. c | Time t h | Conv. in %[b] | ee in % |
|---|---|---|---|---|---|---|
| 92. | (S) | $C_6H_5$ | 2 mM | 20 | 69.5 | 68.4 (R) |
| 93. | (S) | $CH(CH_2CH_3)_2$ | 4 mM | 3 | 100 | 87.1 (R) |
| 94. | (S) | $CH(CH_2)_4$ (Cyclopentyl) | 4 mM | 3 | 94.2 | 88.5 (R) |
| 95. | (S) | $C(CH_3)_3$ | 4 mM | 3 | 100 | 82.8 (R) |
| 96. | (S) | (−)-Menthyl | 4 mM | 3 | 100 | 44.9 (R) |
| 97. | (S) | (+)-Menthyl | 4 mM | 3 | 96.0 | 53.0 (R) |

[a]These are ligands of structure I with $R^1 = R^2 = R^3 = R^4 = R^5 = R^6 = R^{1'} = R^{2'} = R^{3'} = R^{4'} = R^{5'} = R^{6'} = H$ and $Y = O$.

[b]If an educt could no longer be detected by gas chromatography, 100% is stated as the conversion.

The invention claimed is:

1. A process for preparing hydrogenated prochiral olefins, ketones or ketimines, said process comprising asymmetrically hydrogenating prochiral olefins, ketones or ketimines in the presence of transition metal catalysts, wherein the transition metal catalysts comprise transition metals and ligands selected from the group consisting of compounds of the formulas I to IV:

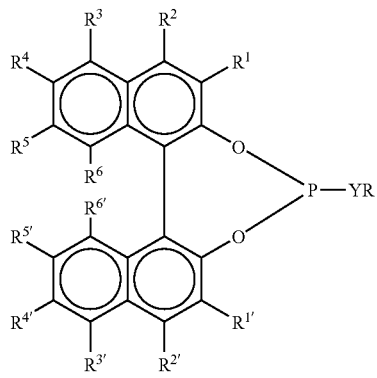

I

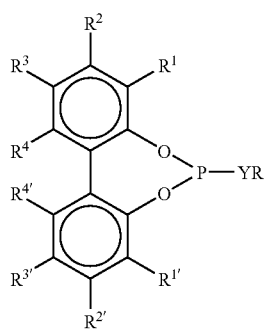

II

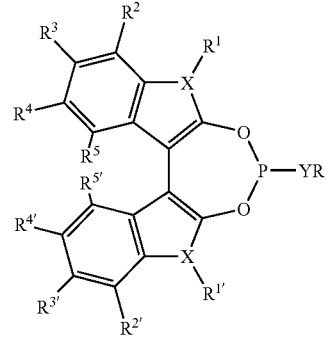

III

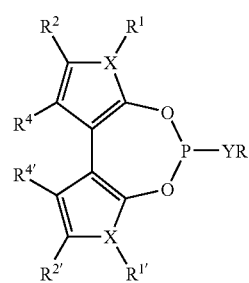

IV wherein Y represents oxygen or sulfur, and R is selected from the group consisting of hydrogen, saturated and unsaturated linear and branched $C_1$ to $C_{50}$ alkyl, $C_1$ to $C_{50}$ aryl and heteroaryl groups;

and $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ are independently selected from the group consisting of hydrogen, halogen, saturated and unsaturated linear and branched $C_1$ to $C_{50}$ alkyl, $C_1$ to $C_{50}$ aryl, $C_1$ to $C_{50}$ heteroaryl, alkynyl, silyl, nitro, nitrile, ester, carboxy, carbonyl, amide, amine, hydroxy, alkoxy, sulfide and selenide groups;

wherein $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ independently may themselves comprise further substituents or be functionalized;

wherein X represents oxygen, sulfur or nitrogen, and wherein, when X=O or X=S, the substituents $R^1$ and $R^{1'}$ are omitted.

2. The process according to claim 1, wherein a ligand of formula I or III is employed.

3. The process according to claim 1, wherein a ligand of formula II or IV is employed, wherein $R^4=R^{4'}=H$ and R is chiral; wherein R is saturated and unsaturated linear and branched $C_1$ to $C_{50}$ alkyl, $C_1$ to $C_{50}$ aryl and heteroaryl groups.

4. The process according to claim 1, wherein a ligand of formula II or IV is employed, wherein $R^4 \neq H$ and $R^{4'} \neq H$.

5. The process according to any one of claims 1-4, wherein said transition metal catalysts contain transition metals of groups VIII and Ib of the Periodic Table.

6. The process according to claim 1, wherein one of the complexes VI to XXIX is employed as the transition metal catalyst:

| [2I·Rh(cod)Z] | [2II·Rh(cod)Z] | [2III·Rh(cod)Z] | [2IV·Rh(cod)Z] |
|---|---|---|---|
| VI | VII | VIII | IX |
| [2I·Ru(cymol)Cl]Z | [2II·Ru(cymol)Cl]Z | [2III·Ru(cymol)Cl Z] | [2IV·Ru(cymol)Cl]Z |
| X | XI | XII | XIII |
| [2I·Ir(cod)Z] | [2II·Ir(cod)Z] | [2III·IR(cod)Z] | [2IV·Ir(cod)Z] |
| XIV | XV | XVI | XVII |
| [2I·Ni(cod)] | [2II·Ni(cod)] | [2III·Ni(cod)] | [2IV·Ni(cod)] |
| XIIX | XIX | XX | XXI |
| [2I·Pd(CH$_3$)$_2$] | [2II·Pd(CH$_3$)$_2$] | [2III·Pd(CH$_3$)$_2$] | [2IV·Pd(CH$_3$)$_2$] |
| XXII | XXIII | XXIV | XXV |
| [2I·Pt(cod)] | [2II·Pt(cod)] | [2III·Pt(cod)] | [2IV·Pt(cod)] |
| XXVI | XXVII | XXIIX | XXIX | wherein
  cod represents $\eta^2,\eta^2$-1,5-cyclooctadiene;
  cymol represents $\eta^6$-1-iso-propyl-4-methylbenzene;
  Z is an anion selected from the group consisting of $BF_4^-$, $BAr_4^-$, $SbF_6^-$ and $PF_6^-$;
  Ar=phenyl or

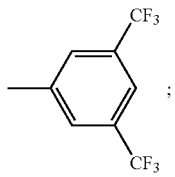

and
  I, II, III and IV represent the ligands of formulas I-IV, respectively, from claim 1.

7. The process according to claim 6, wherein a ligand of formula I or III is employed.

8. The process according to claim 6, wherein a ligand of formula II or IV is employed, wherein $R^4=R^{4'}=H$ and R is chiral; wherein R is saturated and unsaturated linear and branched $C_1$ to $C_{50}$ alkyl, $C_1$ to $C_{50}$ aryl and heteroaryl groups.

9. The process according to claim 6, wherein a ligand of formula II or IV is employed, wherein $R^4 \neq H$ and $R^{4'} \neq H$.

10. The process according to any one of claims 6-9, wherein said transition metal catalysts contain transition metals of groups VIII and Ib of the Periodic Table.

* * * * *